US010215732B2

(12) United States Patent
Shinada

(10) Patent No.: US 10,215,732 B2
(45) Date of Patent: Feb. 26, 2019

(54) DIELECTRIC BARRIER DISCHARGE IONIZATION DETECTOR

(71) Applicant: Shimadzu Corporation, Kyoto (JP)

(72) Inventor: Kei Shinada, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/698,391

(22) Filed: Sep. 7, 2017

(65) Prior Publication Data

US 2018/0067081 A1 Mar. 8, 2018

(30) Foreign Application Priority Data

Sep. 8, 2016 (JP) ................................. 2016-175502

(51) Int. Cl.
*G01N 27/68* (2006.01)
*G01N 30/64* (2006.01)
*G01N 30/02* (2006.01)

(52) U.S. Cl.
CPC ............ *G01N 27/68* (2013.01); *G01N 30/64* (2013.01); *G01N 2030/025* (2013.01)

(58) Field of Classification Search
CPC ... G01N 2030/025; G01N 30/64; G01N 27/68
(Continued)

(56) References Cited

U.S. PATENT DOCUMENTS 4,282,521 A * 8/1981 Lieberman ............ G01M 3/007
200/61.03
2010/0320916 A1 12/2010 Yagi et al.
(Continued)

FOREIGN PATENT DOCUMENTS

| JP | 2010-060354 A | 3/2010 |
|---|---|---|
| JP | 2013-125022 A | 6/2013 |
| WO | 2012/169419 A1 | 12/2012 |

OTHER PUBLICATIONS

Shinada et al., "Development of New Ionization Detector for Gas Chromatography by Applying Dielectric Barrier Discharge", Shimadzu Hyouron (Shimadzu Review), vol. 69, Nos. 3/4, Mar. 29, 2013, pp. 255-263.
(Continued)

*Primary Examiner* — Melissa Koval
*Assistant Examiner* — Trung Nguyen
(74) *Attorney, Agent, or Firm* — Maier & Maier, PLLC

(57) ABSTRACT

A dielectric barrier discharge ionization detector includes: a discharging section for generating plasma from argon-containing gas by electric discharge, including a dielectric tube on the outer wall of which a high-voltage electrode connected to AC power source as well as upstream-side and downstream-side ground electrodes and are circumferentially formed; and a charge-collecting section for ionizing sample-gas components by the plasma and detecting ion current formed by ionized components. The dielectric tube is made of a material whose resistivity is $1.0 \times 10^{13}$ Ωcm or lower. Furthermore, the detector satisfies at least one of the following conditions: the upstream-side ground electrode is longer than a ground electrode length which allows creeping discharge between the high-voltage electrode and a tube-line tip member; or the downstream-side ground electrode is longer than a ground electrode length which allows creeping discharge between the high-voltage electrode and the charge-collecting section.

5 Claims, 8 Drawing Sheets

(58) Field of Classification Search
USPC ...... 324/757.04–762.06, 500, 547, 536, 439,
324/446, 543, 691–727, 66, 678, 76.11,
324/76.32–76.76; 250/281–288, 397,
250/430, 423
See application file for complete search history.

(56) References Cited

U.S. PATENT DOCUMENTS

| | | |
|---|---|---|
| 2011/0316552 A1 | 12/2011 | Shinada et al. |
| 2014/0145724 A1 | 5/2014 | Shinada et al. |
| 2017/0292904 A1* | 10/2017 | Xing .................... G01N 15/088 |
| 2018/0067079 A1 | 3/2018 | Shinada et al. |
| 2018/0067080 A1 | 3/2018 | Shinada et al. |
| 2018/0067082 A1 | 3/2018 | Shinada et al. |
| 2018/0067083 A1 | 3/2018 | Shinada et al. |

OTHER PUBLICATIONS

Office Action dated Nov. 1, 2018 in corresponding U.S. Appl. No. 15/698,312; 12 pages.
Office Action dated Nov. 1, 2018 in corresponding U.S. Appl. No. 15/698,351; 12 pages.
Kogelschatz, Ulrich, "Dielectric-ban-ler Discharges: Their History, Discharge Physics, and Industrial Applications", Plasma Chemistry and Plasma Processing, vol. 23, No. 1, Mar. 2003, 49 pages.

* cited by examiner

DIELECTRIC BARRIER DISCHARGE IONIZATION DETECTOR

TECHNICAL FIELD

The present invention relates to a dielectric barrier discharge ionization detector which is primarily suitable as a detector for a gas chromatograph (GC).

BACKGROUND ART

In recent years, dielectric barrier discharge ionization detectors (which are hereinafter abbreviated as the "BIDs") employing the ionization by dielectric barrier discharge plasma have been put to practical use as a new type of detector for GC (for example, see Patent Literatures 1 and 2 as well as Non Patent Literature 1).

BIDs described in the aforementioned documents are roughly composed of a discharging section and a charge-collecting section which is located below the discharging section. In the discharging section, a low-frequency AC high voltage is applied to plasma-generating electrodes circumferentially formed around a tube made of a dielectric material, such as quartz glass ("dielectric tube"), to ionize an inert gas supplied into the tube line of the dielectric tube and thereby form atmospheric-pressure non-equilibrium plasma. Due to the effects of the light emitted from this plasma (vacuum ultraviolet light), excited species and other elements, the sample components in a sample gas introduced into the charge-collecting section are ionized. The resulting ions are collected through a collecting electrode to generate detection signals corresponding to the amount of ions, i.e. the amount of sample components.

FIG. 8 shows the configuration of the discharging section and surrounding area in the aforementioned BID. As noted earlier, the discharging section 610 includes a cylindrical dielectric tube 611 made of a dielectric material, such as quartz, the inner space of which forms a passage of inert gas serving as plasma generation gas. On the outer wall surface of the cylindrical dielectric tube 611, three ring-shaped metallic electrodes (made of stainless steel, copper or the like) are circumferentially formed at predetermined intervals of space. A high AC excitation voltage power source 615 for generating a low-frequency high AC voltage is connected to the central electrode 612 among the three electrodes, while the electrodes 613 and 614 located above and below the central electrode are both grounded. Hereinafter, the central electrode is called the "high-voltage electrode" 612, while the upper and lower electrodes are respectively called the "ground electrodes" 613 and 614. The three electrodes are collectively referred to as the plasma generation electrodes. Since the wall surface of the cylindrical dielectric tube 611 is present between the passage of the inert gas and the plasma generation electrodes, the dielectric wall itself functions as a dielectric coating layer which covers the surface of those electrodes 612, 613 and 614, enabling a dielectric barrier discharge to occur. With the inert gas flowing through the cylindrical dielectric tube 611, when the high AC excitation voltage power source 615 is energized, a low-frequency high AC voltage is applied between the high-voltage electrode 612 and each of the upper and lower ground electrodes 613 and 614 located above and below. Consequently, an electric discharge occurs within the area sandwiched between the two ground electrodes 613 and 614. This electric discharge is induced through the dielectric coating layer (the wall surface of the cylindrical dielectric tube 611), and therefore, is a form of dielectric barrier discharge, whereby the plasma generation gas flowing through the cylindrical dielectric tube 611 is ionized over a wide area, forming a cloud of plasma (atmospheric-pressure non-equilibrium plasma).

The two ground electrodes 613 and 614 arranged so as to sandwich the high-voltage electrode 612 in between prevents the plasma generated by the electric discharge from spreading into the upstream and downstream sections of the cylindrical dielectric tube 611, whereby the effective plasma generation area is confined to the space between the two ground electrodes 613 and 614.

In the BID, the dielectric material which covers the surface of the plasma generation electrodes in the previously described manner prevents an emission of thermions or secondary electrons from the surface of the metallic electrodes. Furthermore, since the plasma generated by the dielectric barrier discharge is a non-equilibrium plasma with low-temperature neutral gas, various factors which cause a fluctuation of the plasma are suppressed, such as a temperature fluctuation in the discharging section or an emission of gas from the inner wall of the quartz tube due to the heat. As a result, the BID can maintain plasma in a stable form and thereby achieve a higher level of signal-to-noise (SN) ratio than the flame ionization detector (FID), which is the most commonly used type of detector for GC.

In general, there are two types of "dielectric barrier discharge": an electric discharge generated by a configuration in which only one of the high-voltage and ground electrodes is covered with a dielectric body (which is hereinafter called the "single-side barrier discharge"); and an electric discharge generated by a configuration in which both of the high-voltage and ground electrodes are covered with a dielectric body (which is hereinafter called the "double-side barrier discharge". Non Patent Literature 1 discloses the result of a study in which two discharging sections respectively employing those two configurations were constructed and their detector outputs in a BID-equivalent structure were compared, which demonstrated that a higher SN ratio could be achieved with the double-side barrier discharge than with the single-side barrier discharge.

As the inert gas for plasma generation in such a BID, helium (He) gas or argon (Ar) gas (or He gas with a trace amount of Ar gas added) is particularly widely used in practice. The reasons for using those gases are as follows:

(1) He gas: The discharge light generated by using He gas has an extremely high energy level of approximately 17.7 eV, making it possible to ionize and detect the atoms and molecules of most substances except for neon (Ne) and He. This is particularly useful for the detection of inorganic substances, since FIDs cannot ionize (and therefore cannot detect) inorganic substances.

(2) Ar gas (or He gas with a trace amount of Ar gas added): The energy level of discharge light generated by using Ar gas is approximately 11.7 eV and cannot ionize inorganic substances, as with the FID. This characteristic is useful in the case of specifically detecting organic substances. For example, in the case of detecting a trace amount of organic substance in an aqueous solution, the trace amount of organic substance of interest can be easily detected since the water used as the solvent cannot be detected.

Since the discharge characteristics vary depending on the kind of gas, the optimum electrode arrangement (e.g. the width of each electrode and the spacing of the electrodes) in the discharging section of the BID also changes depending on whether He gas or Ar gas is used as the inert gas. Accordingly, BIDs are configured to allow users to prepare a plurality of cylindrical dielectric tubes with different electrode arrangements and select a cylindrical dielectric tube having a suitable electrode arrangement for the kind of gas to be used. In the following description, a BID which uses Ar gas (or He gas with a trace amount of Ar gas added) as the plasma generation gas is called the "Ar-BID". Similarly, a BID which uses lie gas as the plasma generation gas is called the "He-BID".

FIG. 9 is a graph obtained by plotting the discharge initiation voltage for He and Ar at atmospheric pressure against the inter-electrode distance based on Paschen's law which is an empirical law concerning the discharge voltage for spark discharge. As can be seen in the graph, when the inter-electrode distance is the same, the discharge initiation voltage for Ar is approximately two times as high as the discharge initiation voltage for lie. In other words, provided that the device should be operated at the same discharge initiation voltage, the inter-electrode distance for Ar needs to be equal to or shorter than one half of the distance for He. Since there are also other parameters affecting the dielectric barrier discharge employed in BIDs, such as the material of the dielectric body, gas purity, frequency of the discharge power source, and waveform of the power source, it is difficult to predict an optimum electrode arrangement and discharging conditions from Paschen's law which is the empirical law concerning spark discharge. However, from the foregoing discussion, it is at least possible to conclude that the Ar-BID requires a shorter inter-electrode distance between the plasma generation electrodes (or a higher discharge voltage) than the He-BID.

CITATION LIST

Patent Literature

Patent Literature 1: JP 2010-60354 A
Patent Literature 2: WO 2012/169419 A
Patent Literature 3: JP 2013-125022 A Non Patent Literature Non Patent Literature 1: Shinada and four other authors, "Development of New Ionization Detector for Gas Chromatography by Applying Dielectric Barrier Discharge", Shimac Hyouron (Shimadzu Review), Vol. 69, Nos. 3/4, Mar. 29, 2013

SUMMARY OF INVENTION

Technical Problem

Due to the previously described reason, the distance between the neighboring electrodes in conventional Ar-BIDs has been made shorter than in He-BIDs. However, an Ar-BID configured in this manner has an evidently lower SN ratio than He-BIDs.

A study to search for the cause of such a decrease in the SN ratio in the Ar-BID has experimentally revealed the fact that, in the case of the electric discharge in Ar gas, although the inter-electrode distance at which the electric discharge can occur is short as noted earlier, once the electric discharge is initiated, the plasma generation area spreads over the entire cylindrical dielectric tube 611 and eventually reaches the tube-line tip member 616 provided at the upper end of the cylindrical dielectric tube 611 as well as the connection member 621 of the charge-collecting section connected to the lower end of the cylindrical dielectric tube 611. Since the tube-line tip member 616 and the connection member 621 are both made of metal and electrically grounded, the electric discharge which occurs within the cylindrical dielectric tube 611 in the aforementioned situation becomes a single-side barrier discharge between the high-voltage electrode 612 which is covered with the dielectric body and the tube-line tip member 616 or connection member 621 which is not covered with any dielectric body. This is the likely reason why the SN ratio was lower than in the case of the double-side barrier discharge.

The present invention has been developed in view of the previously described point. Its objective is to prevent the occurrence of a single-side barrier discharge in the Ar-BID and thereby achieve a high SN ratio.

Solution to Problem

The present inventor has inferred that the aforementioned expansion of the plasma generation area beyond the range estimated by Paschen's law occurs due to the creeping discharge occurring at the interface between the inner wall of the cylindrical dielectric tube 611 and the Ar gas. Creeping discharge is a discharge phenomenon which occurs along the boundary surface between different dielectrics. In Ar-BIDs, it is likely that this phenomenon develops from the high-voltage electrode 612 into the upper and lower areas, to eventually induce a gas discharge between the high-voltage electrode 612 and the tube-line tip member 616 as well as between the high-voltage electrode 612 and the charge-collecting section. That is to say, in the aforementioned Ar-BID, since the tube-line tip member 616 or the metallic member (connection member 621) near the upper end of the charge-collecting section is electrically grounded, a potential gradient is formed from the high-voltage electrode 612 toward each of those members 616 and 621. If the ground electrodes 613 and 614 provided between the high-voltage electrode 612 and each of those members 616 and 621 are sufficiently long, the reference potential is spread over a wide range within the space between the high-voltage electrode 612 and each of those members 616 and 621, preventing the development of the creeping discharge. However, in the previously described conventional Ar-BID, since the ground electrodes 613 and 614 are not sufficiently long, the creeping discharge originating from the high-voltage electrode 612 can develop beyond the areas where the ground electrodes 613 and 614 are located, to eventually reach the tube-line tip member 616 or the charge-collecting section, causing the aforementioned expansion of the plasma generation area. Based on such an inference, the present inventor has compared the ground electrode length which allows creeping discharge in the Ar gas and the same length in the lHe gas. The result confirmed that the length in the Ar gas was longer (i.e. the creeping discharge could occur at a longer distance between the high-voltage electrode 612 and each of the members 616 and 621).

Given this result, the present inventor measured the SN ratio in each case where only one of the ground electrodes 613 and 614 above and below the high-voltage electrode 612 was made longer than the conventional ones. The result demonstrated that the SN ratio particularly improved when the downstream-side ground electrode 614 was made longer. A likely reason for this improvement is that, if the creeping discharge occurs in the downstream area of the flow of the plasma generation gas, i.e. in the area near the charge-collecting section, and causes the plasma generation area to expand into the downstream area, the collecting electrode provided for detecting the ion current in the charge-collecting section suffers from the mixing of electromagnetic noise due to the high voltage or an incidence of charged particles from the plasma.

These facts suggest that, in order to prevent the creeping discharge in an Ar-BID, it is beneficial to make the ground electrodes, and particularly the one located on the downstream side of the high-voltage electrode, longer than the ground electrode length which allows creeping discharge in the Ar-BID. However, as shown in FIG. 10, increasing the length of a ground electrode requires increasing the length of the dielectric tube 711 to which the ground electrode 714 is attached, which consequently increases the entire size of the detector. In BIDs, since the charge-collecting section is normally heated to 200° C. or higher temperatures to maintain the sample gas in the gasified state, increasing the detector size leads to an increase in the degree of non-uniformity in the temperature within the dielectric tube, which causes a fluctuation of the output signal.

Thus, a dielectric barrier discharge ionization detector according to the first aspect of the present invention developed for solving the previously described problem is a dielectric barrier discharge ionization detector for ionizing and detecting a sample component in a sample gas by using plasma induced by an electric discharge within a gas passage through which a plasma generation gas containing argon is passed, the detector including:

a) a high-voltage electrode having a surface which faces the gas passage and is covered with a dielectric body;

b) a ground electrode electrically connected to a ground and arranged so as to face the gas passage, the ground electrode having a surface which faces the gas passage and is covered with a dielectric body, with at least a portion of the surface being located downstream of the high-voltage electrode in the flow direction of the plasma generation gas:

c) an AC power source connected to the high-voltage electrode, for applying an AC voltage between the high-voltage electrode and the ground electrode so as to induce a dielectric barrier discharge within the gas passage and thereby generate plasma; and d) a charge-collecting section forming a section of the gas passage and located downstream of the ground electrode, including a sample-gas introducer for introducing a sample gas into the downstream section and a collecting electrode for collecting ions generated from a sample component in the sample gas by light emitted from the plasma, where:

the bulk resistivity or surface resistivity of the dielectric body covering the high-voltage electrode is equal to or lower than $1.0 \times 10^{13}$ Ωcm; and the length of the ground electrode on the downstream side of the high-voltage electrode is longer than the ground electrode length which allows creeping discharge between the high-voltage electrode and the charge-collecting section.

The "ground electrode length which allows creeping discharge between the high-voltage electrode and the charge-collecting section" means the largest length of the ground electrode which allows the creeping discharge to occur between the high-voltage electrode and the ground electrode under the condition that the ground electrode covered with a dielectric body is located between the high-voltage electrode and the charge-collecting section (the same applies below). For example, in the Ar-BID having the discharging section 610 as shown in FIG. 8 in which the ground electrode 614 is arranged between the high-voltage electrode 612 and the charge-collecting section located downstream of the discharging section 610, if the length of the ground electrode 614 is gradually decreased while the high AC excitation voltage power source 615 is energized, a creeping discharge begins at a certain length, causing a sudden increase in the current value as measured between the high-voltage electrode 612 and the charge-collecting section (e.g. the connection member 621). The length of the ground electrode 614 at which such a sudden increase in the current value occurs is the ground electrode length which allows creeping discharge During the development of the creeping discharge on the surface of a dielectric body, the ionization actively occurs at its front end, forming a highly conductive path behind. However, if the dielectric body has a low resistivity, the electric charges resulting from the ionization are rapidly diffused through the dielectric body. Therefore, the aforementioned highly conductive path will not be formed and the creeping discharge will not easily develop. Accordingly, the development of the creeping discharge from the high-voltage electrode toward the charge-collecting section can be impeded by using, as the dielectric body covering the high-voltage electrode, a dielectric body whose bulk resistivity or surface resistivity is lower than that of a conventional one, or specifically, a dielectric body having a bulk resistivity or surface resistivity equal to or lower than $1.0 \times 10^{13}$ Ωcm at ordinary temperature (about 20° C.), as in the present invention. As a result, the ground electrode length which allows creeping discharge within the area between the high-voltage electrode and the charge-collecting section becomes shorter than in the conventional case. Therefore, making the ground electrode longer than the ground electrode length which allows creeping discharge does not cause a significant increase in the detector size. That is to say, in the dielectric barrier discharge ionization detector according to the present invention, it is possible to prevent an occurrence of the creeping discharge while minimizing the increase in the detector size.

The ground electrode length which allows creeping discharge depends on the resistivity of the dielectric body as well as such parameters as the frequency and amplitude of the low-frequency AC voltage, waveform of the power source, and property of gas (gas purity). Therefore, the "the length of the ground electrode on the downstream side of the high-voltage electrode" in the present invention should be determined according to those parameters to be applied when the Ar-BID is in use.

The dielectric barrier discharge ionization detector according to the present invention is not limited to a configuration as shown in FIG. 8 in which a high-voltage electrode 612 and two ground electrodes 613 and 614 are circumferentially formed on the outer circumferential surface of a cylindrical dielectric tube 611; it can be applied in various structures of the dielectric barrier discharge ionization detectors. For example, the present invention can also be applied in a dielectric barrier discharge ionization detector disclosed in Patent Literature 3 (a schematic configuration of which is shown in FIG. 11), which includes a high-voltage electrode 812 circumferentially formed on the outer circumferential surface of an external dielectric tube 811 and an electrode structure 834 inserted into the external dielectric tube 811, the electrode structure 834 including an electrically grounded metallic tube 832 (which corresponds to the ground electrode in the present invention) covered with an internal dielectric tube 831 (this example will be detailed later).

When the present invention is applied in the dielectric barrier discharge ionization detector as shown in FIG. 8, the cylindrical dielectric tube 611 corresponds to both the dielectric body covering the high-voltage electrode and the dielectric body covering the ground electrode in the present invention. In other words, these dielectric bodies are formed as a single component. When the present invention is applied in the dielectric barrier discharge ionization detector as shown in FIG. 11, the external dielectric tube 811 corresponds to the dielectric body covering the high-voltage electrode in the present invention, while the internal dielectric tube 831 corresponds to the dielectric body covering the ground electrode in the present invention. In other words, these dielectric bodies are formed as separate components.

As noted earlier, in the dielectric barrier discharge ionization detector, as shown in the example of FIG. 8, the tube-line tip member 616 provided at the upper end of the discharging section 610 is also made of metal and electrically grounded. Therefore, the creeping discharge originating from the high-voltage electrode 612 can develop into both upstream and downstream sides.

Accordingly, the dielectric barrier discharge ionization detector according to the first aspect of the present invention may be modified into a dielectric barrier discharge ionization detector for ionizing and detecting a sample component in a sample gas by using plasma induced by an electric discharge within a gas passage through which a plasma generation gas containing argon is passed, the detector including:

a) a dielectric tube made of a dielectric material and containing an upstream section of the gas passage;

b) an electrically grounded tube-line tip member made of metal, for introducing the plasma generation gas into the dielectric tube;

c) a high-voltage electrode attached to the outer wall of the dielectric tube;

d) an electrically grounded upstream-side ground electrode attached to the outer wall of the dielectric tube and located upstream of the high-voltage electrode as well as downstream of the tube-line tip member in the flow direction of the plasma generation gas;

e) an electrically grounded downstream-side ground electrode attached to the outer wall of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:

the bulk resistivity or surface resistivity of the dielectric body covering the high-voltage electrode is equal to or lower than $1.0 \times 10^{13}$ Ωcm; and one or both of the following conditions are satisfied: the length of the upstream-side ground electrode in the flow direction is longer than the ground electrode length which allows creeping discharge between the tube-line tip member and the high-voltage electrode; or the length of the downstream-side ground electrode in the flow direction is longer than the ground electrode length which allows creeping discharge between the high-voltage electrode and the charge-collecting section.

For the purpose of improving the SN ratio, it is preferable make both of the upstream-side and downstream-side ground electrodes longer than the ground electrode length which allows creeping discharge on the upstream and downstream sides of the high-voltage electrode, respectively. However, it causes some problems, such as an increase in the entire length of the dielectric tube, as well as the necessity to supply a considerably high voltage from the AC power source since a configuration for completely preventing the creeping discharge also impedes the intended electric discharge between the high-voltage electrode and each of the upper and lower ground electrodes. Accordingly, the configuration in which only one of the ground electrodes is made longer also has practical merits.

It is also possible to form the surface of the dielectric body uneven so as to increase the creepage distance (the shortest distance as measured along the surface of the dielectric body) between the high-voltage electrode and the charge-collecting section, and thereby shorten the ground electrode length which allows creeping discharge.

Thus, a dielectric barrier discharge ionization detector according to the second aspect of the present invention developed for solving the previously described problem is a dielectric barrier discharge ionization detector for ionizing and detecting a sample component in a sample gas by using plasma induced by an electric discharge within a gas passage through which a plasma generation gas containing argon is passed, the detector including:

a) a dielectric tube made of a dielectric material and containing an upstream section of the gas passage;

b) a high-voltage electrode attached to the outer wall of the dielectric tube;

c) a ground electrode electrically connected to a ground and arranged so as to face the gas passage, the ground electrode having a surface which faces the gas passage and is covered with a dielectric body, with at least a portion of the surface being located downstream of the high-voltage electrode in the flow direction of the plasma generation gas;

d) an AC power source connected to the high-voltage electrode, for applying an AC voltage between the high-voltage electrode and the ground electrode so as to induce a dielectric barrier discharge within the gas passage and thereby generate plasma; and e) a charge-collecting section forming a downstream section of the gas passage and located downstream of the ground electrode, including a sample-gas introducer for introducing a sample gas into the downstream section and a collecting electrode for collecting ions generated from a sample component in the sample gas by light emitted from the plasma, where:

an unevenness is formed on the inner wall of the dielectric tube over an area where the high-voltage electrode is attached and/or an area located downstream of the aforementioned area and upstream of the charge-collecting section; and the length of the ground electrode on the downstream side of the high-voltage electrode is longer than the ground electrode length which allows creeping discharge between the high-voltage electrode and the charge-collecting section.

The dielectric barrier discharge ionization detector according to the second aspect of the present invention may be modified into a dielectric barrier discharge ionization detector for ionizing and detecting a sample component in a sample gas by using plasma induced by an electric discharge within a gas passage through which a plasma generation gas containing argon is passed, the detector including:

a) a dielectric tube made of a dielectric material and containing an upstream section of the gas passage;

b) an electrically grounded tube-line tip member made of metal, for introducing the plasma generation gas into the dielectric tube;

c) a high-voltage electrode attached to the outer wall of the dielectric tube;

d) an electrically grounded upstream-side ground electrode attached to the outer wall of the dielectric tube and located upstream of the high-voltage electrode as well as downstream of the tube-line tip member in the flow direction of the plasma generation gas;

e) an electrically grounded downstream-side ground electrode attached to the outer wall of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:

an unevenness is formed on the inner wall of the dielectric tube over an area where the high-voltage electrode is attached and/or an area located downstream of the aforementioned area and upstream of the charge-collecting section; and the length of the downstream-side ground electrode is longer than the ground electrode length which allows creeping discharge between the high-voltage electrode and the charge-collecting section.

The dielectric barrier discharge ionization detector according to the second aspect of the present invention may be modified into a dielectric barrier discharge ionization detector for ionizing and detecting a sample component in a sample gas by using plasma induced by an electric discharge within a gas passage through which a plasma generation gas containing argon is passed, the detector including:

a) a dielectric tube made of a dielectric material and containing an upstream section of the gas passage;

b) an electrically grounded tube-line tip member made of metal, for introducing the plasma generation gas into the dielectric tube;

c) a high-voltage electrode attached to the outer wall of the dielectric tube;

d) an electrically grounded upstream-side ground electrode attached to the outer wall of the dielectric tube and located upstream of the high-voltage electrode as well as downstream of the tube-line tip member in the flow direction of the plasma generation gas;

e) an electrically grounded downstream-side ground electrode attached to the outer wall of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:

an unevenness is formed on the inner wall of the dielectric tube over an area where the high-voltage electrode is attached and/or an area located upstream of the aforementioned area and downstream of the tube-line tip member; and the length of the upstream-side ground electrode is longer than the ground electrode length which allows creeping discharge between the high-voltage electrode and the tube-line tip member.

Advantageous Effects of the Invention

As described to this point, the dielectric barrier discharge ionization detectors (Ar-BIDs) according to the present invention configured in the previously described manner can suppress an occurrence of the creeping discharge and thereby prevent an expansion of the plasma generation area. As a result, the generation of the single-side barrier discharge mentioned earlier is prevented and the SN ratio is improved.

DESCRIPTION OF EMBODIMENTS

Modes for carrying out the present invention are hereinafter described using embodiments.

First Embodiment

Figure 1:
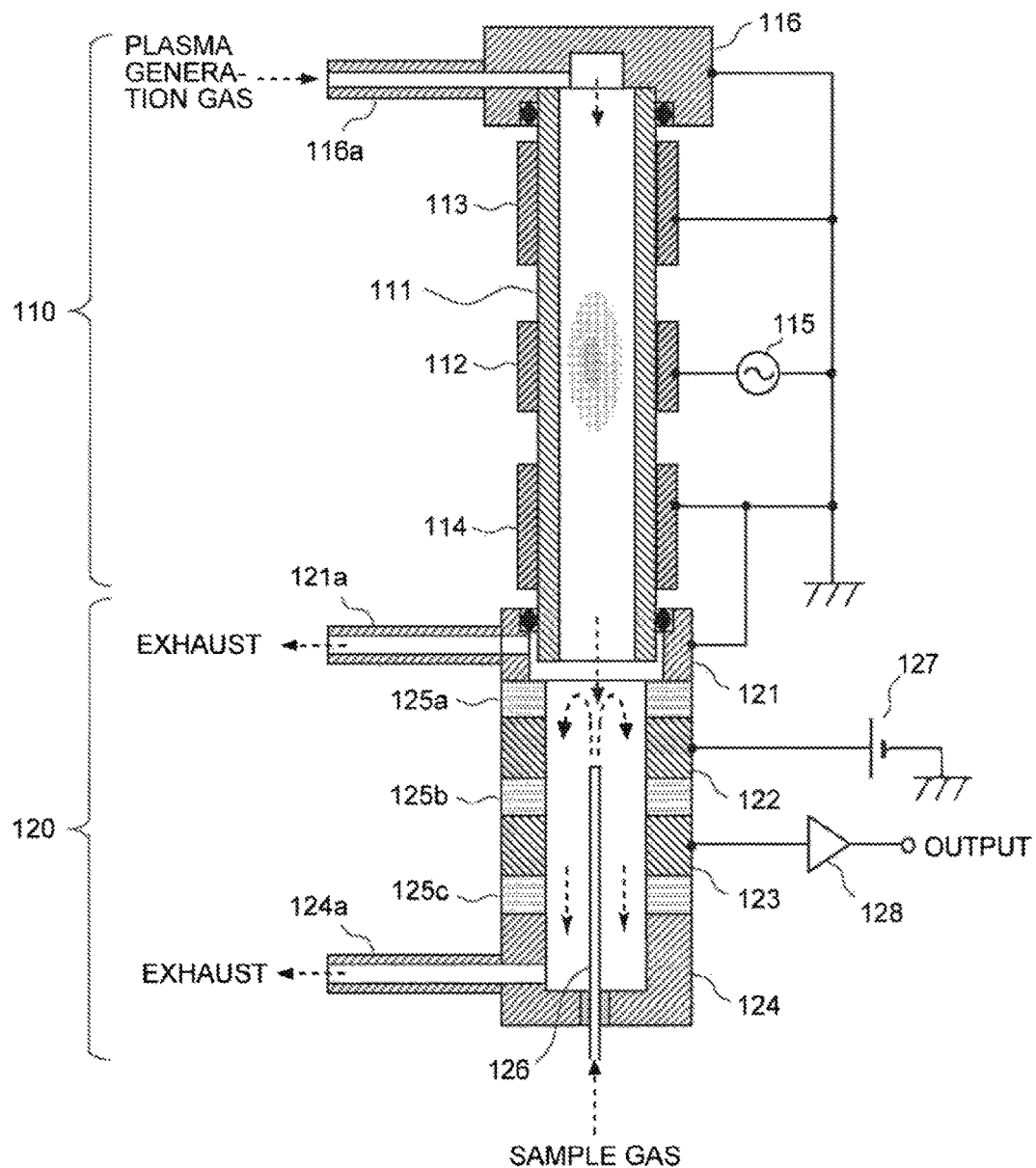
FIG. 1 is a schematic configuration diagram of an Ar-BID according to the first embodiment of the present invention.

FIG. 1 is a schematic configuration diagram of an Ar-BID according to the first embodiment of the present invention.

The Ar-BID of the present embodiment includes a cylindrical dielectric tube 111 through which a plasma generation gas is passed. In the following description, for convenience of explanation, the vertical direction is defined in such a manner that the upstream side in the flow direction of the gas (indicated by the downward arrows in FIG. 1) in the cylindrical dielectric tube 111 is called the "upper" side, and the downstream side is called the "lower" side. However, this definition does not limit the direction in which the Ar-BID should be used.

On the outer wall surface of the cylindrical dielectric tube 111, three ring-shaped electrodes made of an electric conductor (e.g. stainless steel or copper) are circumferentially formed at predetermined intervals of space along the flow direction of the gas.

Among the three electrodes, the central electrode 112 has a high AC excitation voltage power source 115 connected, while the two electrodes 113 and 114 located above and below the electrode 112 are both grounded. Hereinafter, the electrodes 112, 113 and 114 are called the "high-voltage electrode", "upstream-side ground electrode" and "downstream-side ground electrode", respectively, and these electrodes are collectively called the "plasma generation electrodes". The high AC excitation voltage power source 115 generates a high AC voltage at a frequency within a range of 1 kHz-100 kHz, more preferably, approximately 5 kHz-30 kHz (low frequency), with an amplitude of approximately 5 kV-10 kV. The AC voltage may have any waveform, such as a sinusoidal, rectangular, triangular or sawtooth wave.

In the Ar-BID of the present embodiment, the area above the lower end of the downstream-side ground electrode 114 in FIG. 1 is the discharging section 110, and the area below the lower end of the downstream-side ground electrode 114 is the charge-collecting section 120.

The cylindrical dielectric tube 111 has a tube-line tip member 116 at its upper end, to which a gas supply tube 116a is connected. Through this gas supply tube 116a, a plasma generation gas (Ar gas, or He gas with a trace amount of Ar gas added) doubling as a dilution gas is supplied into the cylindrical dielectric tube 111. Since the wall surface of the cylindrical dielectric tube 111 is present between the plasma generation gas and each of the plasma generation electrodes 112, 113 and 114, the wall surface itself functions as the dielectric coating layer which covers the surfaces of the plasma generation electrodes 112, 113 and 114, enabling dielectric barrier discharge to occur, as will be described later.

On the downstream side of the cylindrical dielectric tube 111, a connection member 121, bias electrode 122 and collecting electrode 123, all of which are cylindrical bodies having the same inner diameter, are arranged along the flow direction of the gas, with insulators 125a and 125b made of alumina, PTFE (polytetrafluoronthylene) resin or similar material inserted in between. On the downstream side of the collecting electrode 123, a tube-line end member 124 in the form of a cylindrical body with a closed bottom is attached via an insulator 125c. The inner space formed by the connection member 121, bias electrode 122, collecting electrode 123, tube-line end member 124 and insulators 125a, 125b and 125c communicates with the inner space of the cylindrical dielectric tube 111.

A bypass exhaust tube 121a for exhausting a portion of the plasma generation gas to the outside is connected to the circumferential surface of the connection member 121. A sample exhaust tube 124a is connected to the circumferential surface of the tube-line end member 124. A thin sample introduction tube 126 is inserted through the bottom of the tube-line end member 124. Through this sample introduction tube 126, a sample gas is supplied into the charge-collecting section 120. The charge-collecting section 120 is heated to a maximum temperature of approximately 450° C. by an external heater (not shown) in order to maintain the sample gas in the gasified state.

The connection member 121 is grounded and functions as a recoil electrode for preventing charged particles in the plasma carried by the gas stream from reaching the collecting electrode 123. The bias electrode 122 is connected to a bias DC power source 127. The collecting electrode 123 is connected to a current amplifier 128.

The operation for detecting a sample component contained in a sample gas in the present Ar-BID is hereinafter schematically described. As indicated by the rightward arrow in FIG. 1, a plasma generation gas doubling as a dilution gas is supplied through the gas supply tube 116a into the cylindrical dielectric tube 111. Since the BID according to the present embodiment is an Ar-BID, either an Ar gas or a He gas containing a trace amount of Ar gas is used as the plasma generation gas. The plasma generation gas flows downward through the cylindrical dielectric tube 111, a portion of which is exhausted through the bypass exhaust tube 121a to the outside, while the remaining portion serving as the dilution gas flows downward through the charge-collecting section 120, to be exhausted through the sample exhaust tube 124a to the outside. Meanwhile, the sample gas containing the sample component is supplied through the sample introduction tube 126 and ejected from the sample-gas ejection port at the end of the same tube into the charge-collecting section 120. Although the direction in which the sample gas is ejected from the sample-gas ejection port is opposite to the flow direction of the dilution gas, the sample gas is immediately pushed backward, being merged with the dilution gas and flowing downward, as indicated by the arrows in FIG. 1.

As noted earlier, while the plasma generation gas is flowing through the cylindrical dielectric tube 111, the high AC excitation voltage power source 115 applies a high AC voltage between the high-voltage electrode 112 and the upstream-side ground electrode 113 as well as between the high-voltage electrode 112 and the downstream-side ground electrode 114. As a result, a dielectric barrier discharge occurs within the cylindrical dielectric tube 111, whereby the plasma generation gas is ionized and a cloud of plasma (atmospheric-pressure non-equilibrium plasma) is generated. The excitation light emitted from the atmospheric-pressure non-equilibrium plasma travels through the discharging section 110 and the charge-collecting section 120 to the region where the sample gas is present, and ionizes the sample component in the sample gas. The thereby generated ions move toward the collecting electrode 123 due to the effect of the electric field created by the DC voltage applied to the bias electrode 122. Upon reaching the collecting electrode 123, the ions give electrons to or receive electrons from the same electrode. Consequently, an ion current corresponding to the amount of ions generated from the sample component by the action of the excitation light, i.e. an ion current corresponding to the amount of sample component, is fed to the current amplifier 128. The current amplifier 128 amplifies this current and produces a detection signal. In this manner, the Ar-BID according to the present embodiment produces a detection signal corresponding to the amount (concentration) of the sample component contained in the sample gas introduced through the sample introduction tube 126.

The basic components of the BID in the present embodiment are the same as those of commonly used BIDs. The previously described basic operation for detection is also similar to that of commonly used BIDs. The structural characteristics of the Ar-BID according to the present embodiment exist in that the cylindrical dielectric tube 111 is made of a material whose surface resistivity or bulk resistivity (which are hereinafter simply and collectively referred to as the "resistivity") is lower than that of dielectric materials used in conventional Ar-BIDs (e.g. quartz, sapphire or high-purity alumina), and that the length of the upstream-side ground electrode 113 and that of the downstream-side ground electrode 114 are respectively longer than the ground electrode lengths which allow creeping discharge initiation (between the high-voltage electrode 112 and the tube-line tip member 116 as well as between the high-voltage electrode 112 and the charge-collecting section 120) which depend on the resistivity. The resistivities of quartz, sapphire and high-purity alumina, which have been used as dielectric materials in conventional Ar-BIDs, are all approximately $1.0 \times 10^{14}$ Ωcm at normal temperature (about 20° C.). In the present embodiment, a dielectric material having a lower resistivity than the aforementioned value is used as the material for the dielectric body. Specifically, the cylindrical dielectric tube 111 in the present embodiment is made of a dielectric material whose resistivity at ordinary temperature is equal to or lower than $1.0 \times 10^{13}$ Ωcm. Furthermore, the length of the upstream-side ground electrode 113 (or downstream-side ground electrode 114) is adjusted according to the aforementioned resistivity as well as such parameters as the frequency and amplitude of the low-frequency AC voltage, waveform of the power source and property of gas so that no creeping discharge will occur between the high-voltage electrode 112 and the tube-line tip member 116 (or so that no creeping discharge will occur between the high-voltage electrode 112 and the charge-collecting section 120, or specifically, the connection member 121). As the dielectric material whose resistivity is equal to or lower than $1.0 \times 10^{13}$ Ωcm, for example, an alumina material No. A445 or AH manufactured by Kyocera Corporation can be used.

Figure 10:
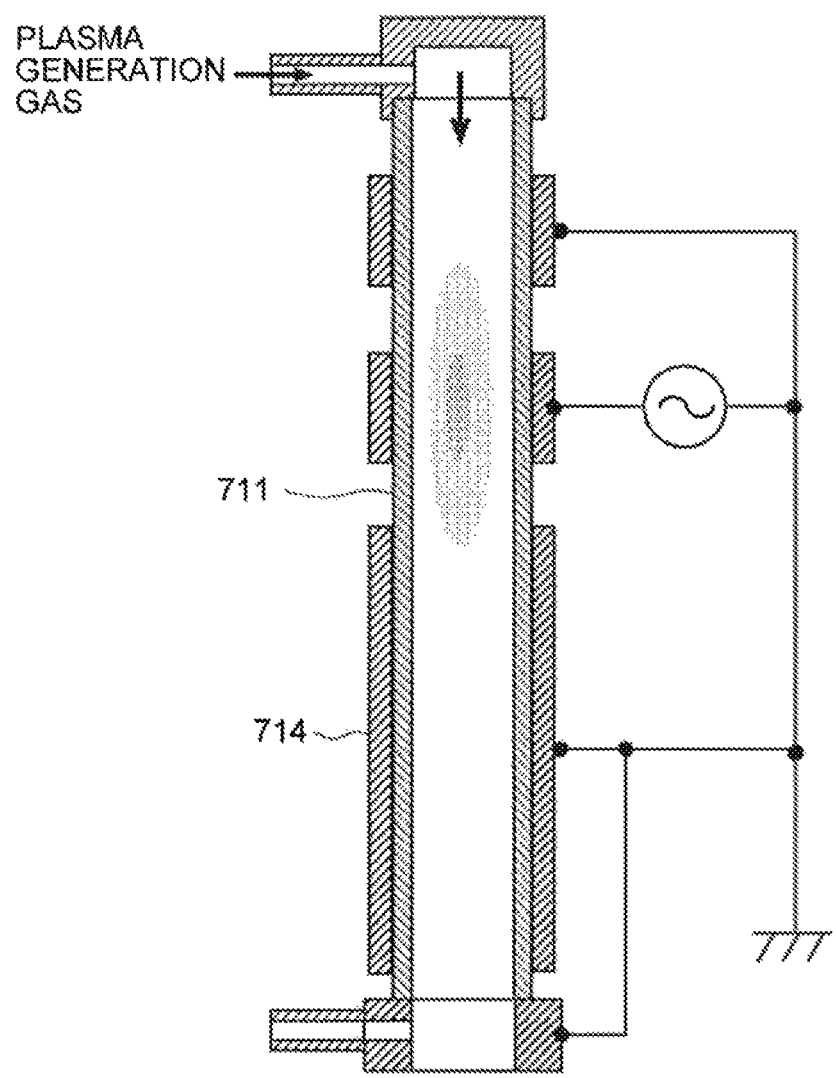
FIG. 10 is a schematic configuration diagram showing a case in which the downstream-side ground electrode of a conventional BID is made longer.

In the Ar-BID according to the present embodiment, by using a dielectric material whose resistivity is lower than that of conventional Ar-BIDs as the material for the cylindrical dielectric tube 111, the ground electrode lengths which allow creeping discharge initiation between the high-voltage electrode 112 and the tube-line tip member 116 as well as between the high-voltage electrode 112 and the charge-collecting section (more specifically, the connection member 121) are made shorter than in an Ar-BID in which a dielectric tube made of quartz glass or the like is used as in the previously described conventional Ar-BID. As a result, the length of the upstream-side ground electrode and that of the downstream-side ground electrode necessary for preventing the creeping discharge also become shorter than in the case of using a conventional dielectric tube made of quartz glass or the like (e.g. FIG. 10). Accordingly, in the Ar-BID according to the present embodiment, it is possible to prevent an occurrence of the creeping discharge and thereby improve the SN ratio while minimizing the increase in the detector size.

In the first embodiment described thus far, both the upstream-side ground electrode 113 and the downstream-side ground electrode 114 are made longer than the respective ground electrode lengths which allow creeping discharge initiation. It is also possible to make only one of them, and particularly, only the downstream-side ground electrode 114, longer than the ground electrode length which allows creeping discharge (between the high-voltage electrode 112 and the charge-collecting section 120).

Second Embodiment

Figure 2:
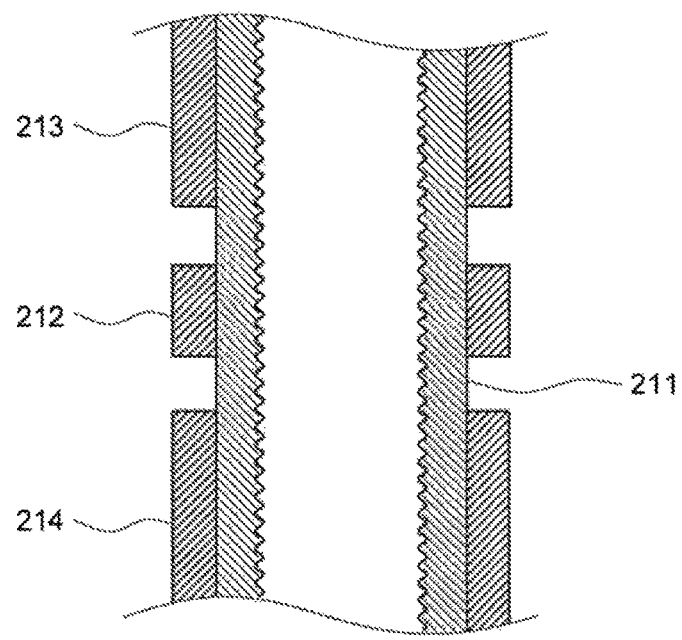
FIG. 2 is a partially enlarged view of an Ar-BID according to the second embodiment of the present invention.
Figure 3:
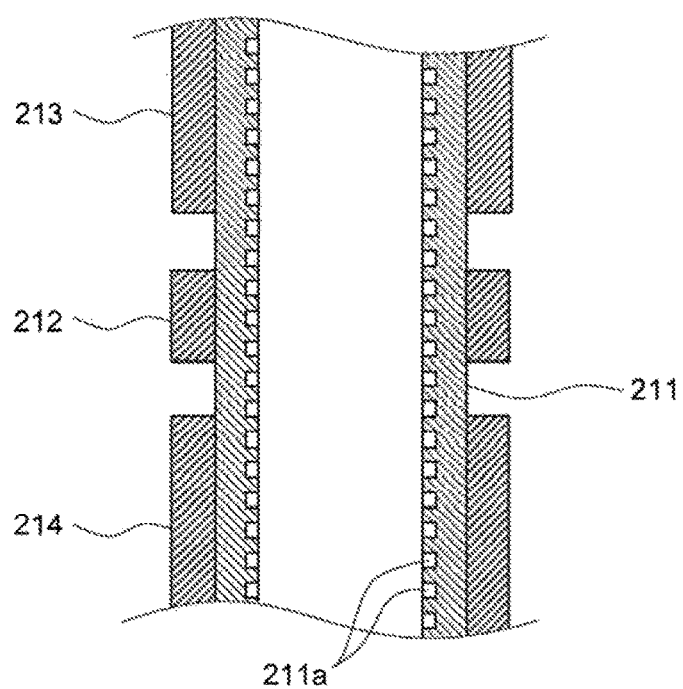
FIG. 3 is a partially enlarged view showing another configuration example of the Ar-BID according to the same embodiment.

FIGS. 2 and 3 are partially enlarged views each of which shows a configuration of the discharging section of the Ar-BID according to the second embodiment of the present invention. The overall configuration of the Ar-BID in the present embodiment is similar to the one shown in FIG. 1 and therefore will not be described.

The configuration of the Ar-BID in the present embodiment is identical to that of the first embodiment except that the ground electrode length which allows creeping discharge between the high-voltage electrode 212 and the charge-collecting section (120 in FIG. 1) and/or between the high-voltage electrode 212 and the tube-line tip member (116 in FIG. 1) is shortened by forming an unevenness on the inner wall surface of the cylindrical dielectric tube 211. The cylindrical dielectric tube 211 may be made of a dielectric material used in conventional Ar-BIDs (quartz, sapphire or high-purity alumina) or a dielectric material having a low resistivity as in the first embodiment.

In order to form the unevenness, the inner wall surface of the cylindrical dielectric tube 211 is roughened in the example of FIG. 2, while a number of grooves 211a extending in a direction orthogonal to the length direction of the cylindrical dielectric tube 211 are formed on the inner wall surface of this cylindrical dielectric tube 211 in the example of FIG. 3. The unevenness needs be formed at least one of the following portions of the cylindrical dielectric tube 211: the inner circumferential surface of the area which covers the high-voltage electrode 212 (this area is hereinafter called the "high-voltage electrode coverage area"); the inner circumferential surface of the area located downstream of the high-voltage electrode coverage area as well as upstream of the charge-collecting section (this area is hereinafter called the "downstream-side area"); and the inner circumferential surface of the area located upstream of the high-voltage electrode coverage area as well as downstream of the tube-line tip member (this area is hereinafter called the "upstream-side area"). More preferably, the unevenness should be formed over the entire range of the inner circumferential surface of the cylindrical dielectric tube 211. When the unevenness is formed on the high-voltage electrode coverage area and/or the downstream-side area, the ground electrode length which allows creeping discharge between the high-voltage electrode 212 and the charge-collecting section becomes shorter. When the unevenness is formed on the high-voltage electrode coverage area and/or the upstream-side area, the ground electrode length which allows creeping discharge between the high-voltage electrode 212 and the tube-line tip member becomes shorter.

In the present embodiment, the length of the downstream-side ground electrode 214 is adjusted according to the number and depth of the unevenness within the high-voltage coverage area and the downstream-side area of the cylindrical dielectric tube 211 (i.e. the creepage distance between the high-voltage electrode 212 and the charge-collecting section) as well as such parameters as the frequency and amplitude of the low-frequency AC voltage, waveform of the power source and property of gas so that no creeping discharge will occur between the high-voltage electrode 212 and the charge-collecting section. Similarly, the length of the upstream-side ground electrode 213 is adjusted according to the number and depth of the unevenness within the high-voltage coverage area and the upstream-side area (i.e. the creepage distance between the high-voltage electrode 212 and the tube-line tip member) as well as the aforementioned parameters so that no creeping discharge will occur between the high-voltage electrode 212 and the tube-line tip member.

In the Ar-BID according to the present embodiment, the ground electrode lengths which allow creeping discharge initiation are shortened by increasing the surface roughness of the inner surface of the cylindrical dielectric tube 211, and after that, the upstream-side ground electrode 213 and the downstream-side ground electrode 214 are made longer than the respective ground electrode lengths which allow creeping discharge initiation so as to prevent the creeping discharge. With this configuration, it is possible to improve the SN ratio while minimizing the increase in the detector size.

In the second embodiment described thus far, both the upstream-side ground electrode 213 and the downstream-side ground electrode 214 are made longer than the respective ground electrode lengths which allow creeping discharge initiation. It is also possible to make only one of them, and particularly, only the downstream-side ground electrode 214, longer than the ground electrode length which allows creeping discharge (between the high-voltage electrode 212 and the charge-collecting section). In the case of making only the downstream-side ground electrode 214 longer than the ground electrode length which allows creeping discharge, the unevenness is formed on the inner circumferential surface of at least either the high-voltage electrode coverage area or the downstream-side area. In the case of making only the upstramn-side ground electrode 213 longer than the ground electrode length which allows creeping discharge, the unevenness is formed on the inner circumferential surface of at least either the high-voltage electrode coverage area or the upstream-side area.

Test Example

Figure 4:
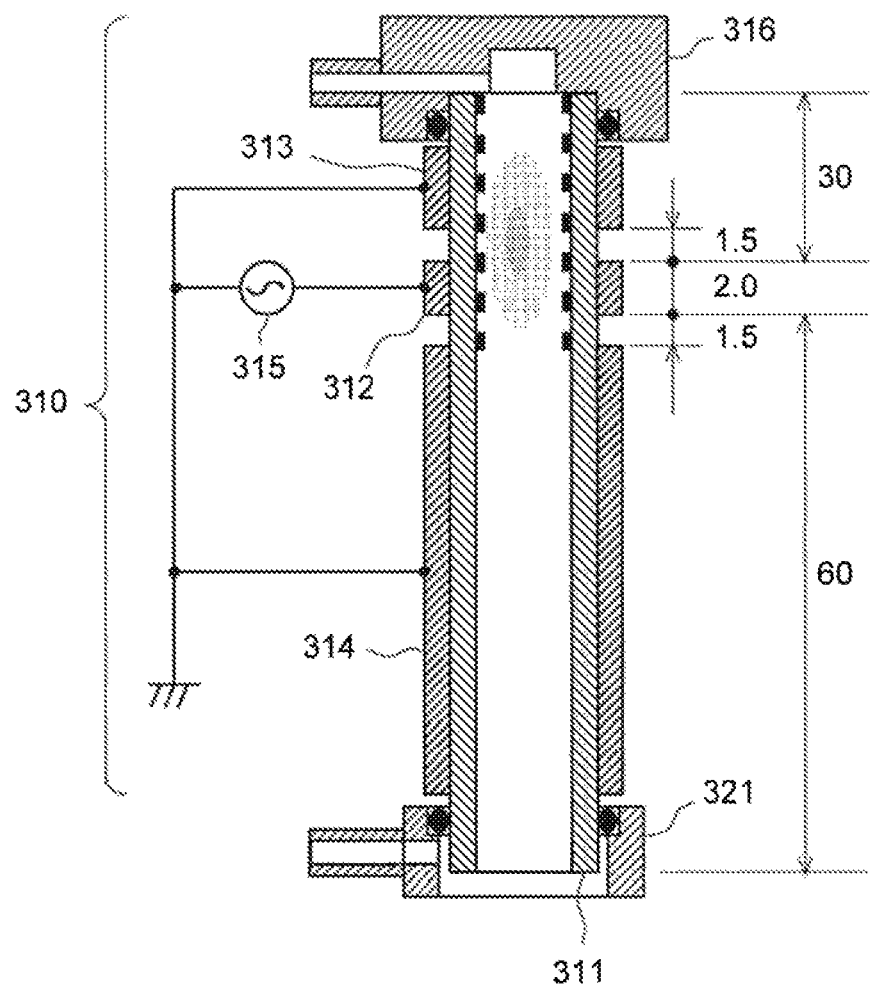
FIG. 4 shows the electrode arrangement in test example 1, test example 2, and comparative example.

Hereinafter described is a test conducted for confirming the effect of the Ar-BIDs according to the first and second embodiments. The test was performed using an Ar-BID including a cylindrical dielectric tube made of the aforementioned alumina No. A445 (which is hereinafter called "test example 1"), Ar-BID including a cylindrical dielectric tube made of quartz with an inner circumferential surface partially worked into a frosted-glass state (which is hereinafter called "test example 2"), and Ar-BID including a cylindrical dielectric tube made of quartz having a smooth inner circumferential surface (which is hereinafter called the "comparative example"). The bulk resistivity of quartz is approximately $1.0 \times 10^{14}$ Ωcm, while that of alumina No. A445 is approximately $1.0 \times 10^{11}$ Ωcm. FIG. 4 shows the electrode arrangement of the discharging section in the Ar-BIDs used in test example 1, test example 2 and comparative example. Only test example 2 had the frosted-glass portion over the area indicated by the broken line in the figure. In any of the test and comparative examples, the cylindrical dielectric tube 311 had an outer diameter of 4 mm, an inner diameter of 2 mm and a length of 92 mm. Strips of copper foil were wound on the outer circumferential surface of the cylindrical dielectric tube 311 to form the high-voltage electrode 312, upstream-side ground electrode 313 and downstream-side ground electrode 314. The electrode arrangement in FIG. 4 was determined so that a creeping discharge would occur on the upstream side of the high-voltage electrode 312 while no creeping discharge would occur on the downstream side when the measurement was performed using the cylindrical dielectric tube prepared for the comparative example as the cylindrical dielectric tube 311 under measurement conditions which will be described later. In other words, the upstream-side ground electrode 313 was shorter than the ground electrode length which allows creeping discharge in the Ar-BID of the comparative example under the aforementioned conditions, while the downstream-side ground electrode 314 was longer than the ground electrode length which allows creeping discharge.

Using each of those Ar-BIDs as the detector for GC, the sensitivity for a solution of a standard sample (dodecane) was measured, with Ar gas (with a degree of purity of 99.9999% or higher) continuously introduced into the cylindrical dielectric tube 311, and the high AC excitation voltage power source 315 energized to apply an AC high voltage having a sinusoidal current waveform at a frequency of approximately 40 kHz with a voltage amplitude of approximately 5 kVp-p. The detection limit was also calculated for each case from the measured noise value. Table 1 below shows the measured results and the calculated results based on the measured results.

TABLE 1

|  | Sensitivity (C/g) | Noise (fA) | Detection Limit (pg/sec) |
| --- | --- | --- | --- |
| Test Example 1 | 0.14 | 14 | 0.20 |
| Test Example 2 | 0.46 | 54 | 0.23 |
| Comparative Example | 0.66 | 93 | 0.28 |

As shown in Table 1, the area sensitivities in test examples 1 and 2 were lower than that in the comparative example. This seems to be due to the fact that the shortened ground electrode length which allows creeping discharge as compared to the comparative example suppresses (not only the creeping discharge developing from the high-voltage electrode 312 into the downstream area but also) the creeping discharge developing into the upstream area, causing the discharge area on the upstream side of the high-voltage electrode 312 to shrink and the amount of discharge light to decrease. However, in the test examples, not only the sensitivity but also the noise value was decreased, with the result that the detection limit was better than in the comparative example. The SN ratio was also higher than in the comparative example. The most likely explanation for this improvement in the SN ratio is that the shrinkage of the discharge area on the upstream side of the high-voltage electrode 312 enabled the electric discharge on the upstream side, which occurs as the single-side barrier discharge in the comparative example, to be a double-side barrier discharge in test examples 1 and 2.

As just described, in test examples 1 and 2, the creeping discharge could be suppressed even on the upstream area where the ground electrode 313 had a relatively short length, and the SN ratio could be consequently improved. Therefore, in the Ar-BID of test example 1, it should be possible to make the downstream-side ground electrode 314 as short as the upstream-side ground electrode 313 and yet prevent the creeping discharge from developing from the high-voltage electrode 312 into the downstream area. Similarly, in the Ar-BID of test example 2, it should be possible to make the downstream-side ground electrode 314 as short as the upstream-side ground electrode 313 and yet prevent the creeping discharge from developing from the high-voltage electrode 312 into the downstream area, if the area provided with the unevenness on the inner wall of the cylindrical dielectric tube 311 is extended into the area located downstream of the high-voltage electrode 312.

As noted earlier, the ground electrode length which allows creeping discharge depends on such parameters as the frequency and amplitude of the low-frequency AC voltage, waveform of the power source, property of gas, and material of the dielectric body. Accordingly, the lengths of the ground electrodes in the Ar-BID according to the present embodiment are not limited to the values shown in FIG. 4, but should be appropriately determined according to the configuration and use conditions of the Ar-BID. For example, under the condition that the various aforementioned parameters are fixed, the length of the downstream-side or upstream-side ground electrode may be variously changed to locate a point at which a sudden change occurs in a specific quantity, such as the size of the plasma generation area, amount of the current flowing between the high-voltage electrode (112 in FIG. 1) and the connection member (121 in FIG. 1), amount of the current flowing between the high-voltage electrode and the tube-line tip member (116 in FIG. 1), or SN ratio during a sample measurement. The length of the ground electrode at the located point can be considered to correspond to the ground electrode length which allows creeping discharge. Therefore, by making the actual length of the downstream-side or upstream-side ground electrode larger than the length corresponding to the aforementioned point, the creeping discharge can be suppressed and a high SN ratio can be achieved. Furthermore, if the length of the ground electrode at which the creeping discharge begins is previously investigated with various values of the aforementioned parameters, it becomes possible to estimate the length of the ground electrode with which a high SN ratio can be achieved under a given condition.

Third Embodiment

Figure 5:
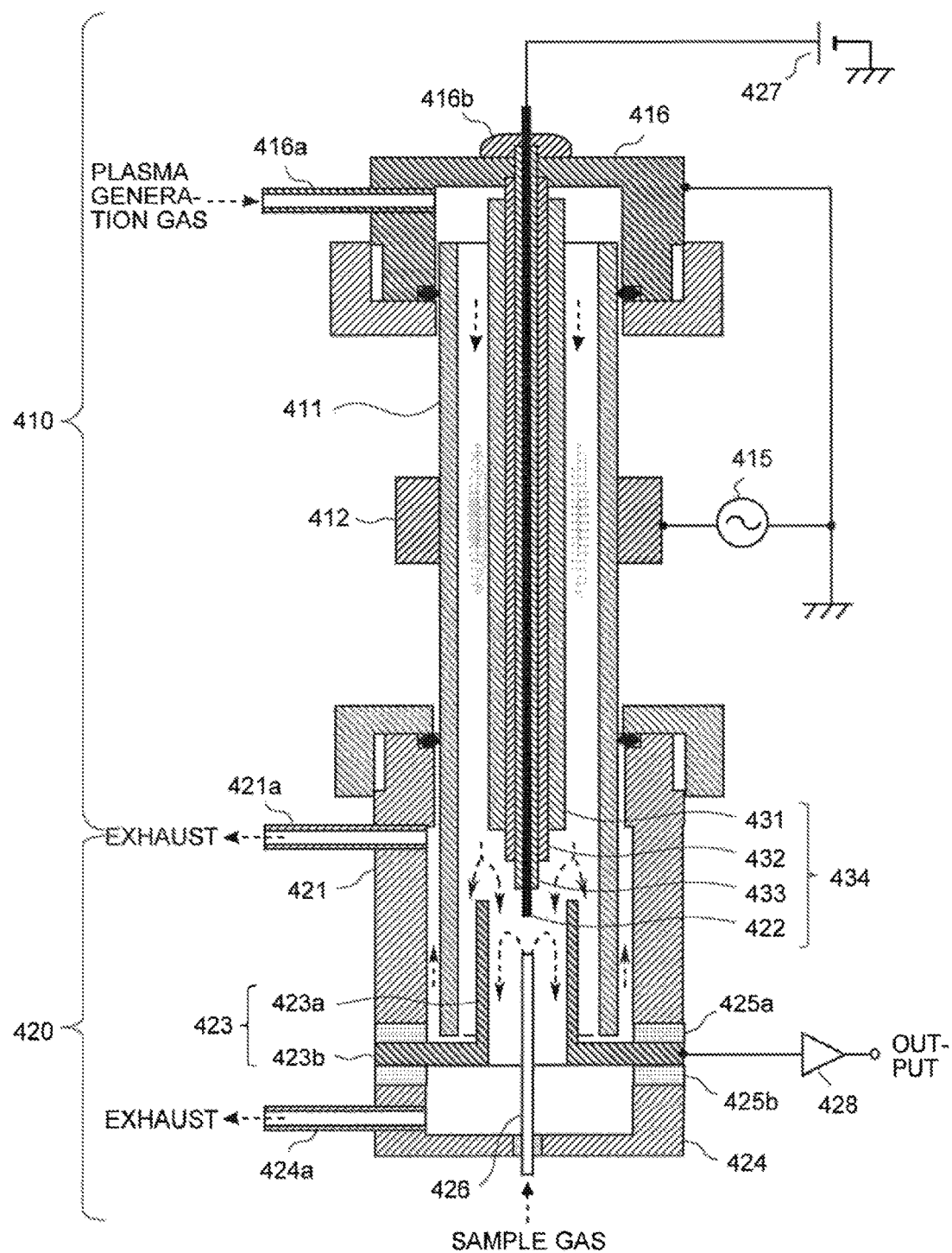
FIG. 5 is a schematic configuration diagram of an Ar-BID according to the third embodiment of the present invention.

The third embodiment of the Ar-BID according to the present invention is hereinafter described with reference to FIG. 5. FIG. 5 is a schematic configuration diagram of the Ar-BID according to the present embodiment.

The Ar-BID of the present embodiment includes an external dielectric tube 411. For example, a dielectric tube measuring 7 mm in outer diameter and 5 mm in inner diameter can be used as the external dielectric tube 411. A ring-shaped electrode 412 made of metal (e.g. stainless steel or copper) is circumferentially formed on the outer circumferential surface of the external dielectric tube 411.

At the upper end of the external dielectric tube 411, a tube-line tip member 416 having a cylindrical shape with a closed top and an open bottom is attached. A gas supply tube 416a is connected to the circumferential surface of the tube-line tip member 416. The tube-line tip member 416 and the supply tube 416a are made of metal, such as stainless steel.

Inside the external dielectric tube 411, an internal dielectric tube 431 made of a dielectric material is arranged, and a metallic tube 432 made of metal (e.g. stainless steel) is inserted into this internal dielectric tube 431. Furthermore, an insulating tube 433 made of alumina or the like is inserted into the metallic tube 432, and a metallic wire 422 made of metal (e.g. stainless steel) is inserted into the insulating tube 433. The internal dielectric tube 431, metallic tube 432, insulating tube 433 and metallic wire 422 have their respective lengths sequentially increased in the mentioned order, with the upper and lower ends of the metallic tube 432 protruding from the upper and lower ends of the internal dielectric tube 431, and the upper and lower ends of the insulating tube 433 protruding from the upper and lower ends of the metallic tube 432. The upper and lower ends of the metallic wire 422 also protrude from the upper and lower ends of the insulating tube 433. The structure composed of the internal dielectric tube 431, metallic tube 432, insulating tube 433 and metallic wire 422 is hereinafter called the "electrode structure 434".

The tube-line tip member 416 has a through hole formed in its upper portion. The upper end of the metallic tube 432 is fixed in this through hole by welding or soldering. The insulating tube 433 and the metallic wire 422 are extracted to the outside from the through hole in the upper portion of the tube-line tip member 416, and sealed and fixed on the upper surface of the tube-line tip member 416 with a gas-tight adhesive 416b.

The tube-line tip member 416 is electrically grounded through an electric line (or gas supply tube 416a), whereby the metallic tube 432 is also electrically grounded via the tube-line tip member 416. On the other hand, the ring-shaped electrode 412 has a high AC excitation voltage power source 415 connected to it. That is to say, in the Ar-BID of the present embodiment, the ring-shaped electrode 412 corresponds to the high-voltage electrode in the present invention, the area of the metallic tube 432 covered with the internal dielectric tube 431 (this area is hereinafter called the "dielectric coverage area") corresponds to the ground electrode in the present invention, and the ring-shaped electrode (high-voltage electrode) 412 and the dielectric coverage area of the metallic tube 432 (ground electrode) function as the plasma generation electrodes. The inner circumferential surface of the ring-shaped electrode 412 faces a portion of the outer circumferential surface of the metallic tube 432 across the wall surfaces of the external dielectric tube 411 and the internal dielectric tube 431. Accordingly, those dielectric wall surfaces themselves function as dielectric coating layers which cover the surfaces of the plasma generation electrodes (i.e. ring-shaped electrode 412 and metallic tube 432), enabling a dielectric barrier discharge to occur.

In the present embodiment, the area above the lower end of the internal dielectric tube 431 in FIG. 5 corresponds to the discharging section 410, and the area below the lower end of the internal dielectric tube 431 corresponds to the charge-collecting section 420.

The lower end of the external dielectric tube 411 is inserted into the cylindrical connection member 421. A bypass exhaust tube 421a made of metal (e.g. stainless steel) is provided on the circumferential surface of the connection member 421.

Below the connection member 421, there are a cylindrical insulating member 425a, flanged metallic tube 423, cylindrical insulating member 425b, and tube-line end member 424 arranged in the mentioned order. The flanged metallic tube 423 has a cylindrical portion 423a and a flange portion 423b which is formed at the lower end of the cylindrical portion 423a and extends outward in the radial direction of the cylindrical portion 423a. The cylindrical portion 423a has an outer diameter smaller than the inner diameter of the external dielectric tube 411 and is inserted in the external dielectric tube 411 from below. The flange portion 423b, which has approximately the same outer diameter as those of the connection member 421, insulating members 425a, 425b and tube-line end member 424, is held between the lower end of the connection member 421 and the upper end of the tube-line end member 424 via the insulating members 425a and 425b. The connection member 421, tube-line end member 424 and flanged metallic tube 423 are all made of metal (e.g. stainless steel). The connection member 421, insulating member 425a, flanged metallic tube 423, insulating member 425b, and tube-line end member 424 are each adhered to the neighboring members with a heat-resistant ceramic adhesive.

The tube-line end member 424 is a cylindrical member having an open top and a closed bottom, with a sample exhaust tube 424a made of metal (e.g. stainless steel) connected to its circumferential surface. A through hole is formed in the bottom surface of the tube-line end member 424, and a sample introduction tube 426 connected to the exit end of a GC column (or similar element) is inserted into the through hole. The sample introduction tube 426 is pulled into the cylindrical portion 423a of the flanged metallic tube 423. The upper end (i.e. sample-gas exit port) of the sample introduction tube 426 is located at a vertical position between the upper and lower ends of the cylindrical portion 423a.

As described earlier, a portion which is not covered with the insulating tube 433 ("exposed portion") is provided at the lower end of the metallic wire 422 in the electrode structure 434. The exposed portion is inserted into the cylindrical portion 423a of the flanged metallic tube 423 from above and is located near the upper end of the cylindrical portion 423a. As a result, the exposed portion of the metallic wire 422 is located directly above the sample-gas exit port. Furthermore, the metallic wire 422 is extracted from the tube-line tip member 416 to the outside and connected to a bias DC power source 427. The flanged metallic tube 423 is connected to a current amplifier 428. That is to say, in the Ar-BID of the present embodiment, the exposed portion at the lower end of the metallic wire 422 functions as the bias electrode, while the cylindrical portion 423a of the flanged metallic tube 423 functions as the ion-collecting electrode. Accordingly, the space between the inner wall of the cylindrical portion 423a and the exposed portion of the metallic wire 422 is the effective ion-collecting area.

As noted earlier, the metallic tube 432 included in the electrode structure 434 is grounded via the tube-line tip member 416, and a portion which is not covered with the internal dielectric tube 431 ("exposed portion") is provided at the lower end of the metallic tube 432. This exposed portion is located directly above the flanged metallic tube 423 and functions as a recoil electrode for preventing charged particles in the plasma from reaching the ion-collecting electrode (i.e. the cylindrical portion 423a).

A detecting operation by the present Ar-BID is hereinafter described. As indicated by the rightward arrow in FIG. 5, a plasma generation gas (Ar gas, or He gas containing a trace amount of Ar gas) doubling as a dilution gas is supplied through the gas supply tube 416a into the tube-line tip member 416.

The plasma generation gas doubling as the dilution gas flows downward through the space between the inner wall of the external dielectric tube 411 and the outer wall of the internal dielectric tube 431. At the upper end of the cylindrical portion 423a of the flanged metallic tube 423, a portion of the gas is made to branch off. The branch portion of the plasma generation gas flows downward through the space between the inner wall of the external dielectric tube 411 and the outer wall of the cylindrical portion 423a. At the lower end of the external dielectric tube 411, the flow turns outward, and then upward. After flowing upward through the space between the outer wall of the external dielectric tube 411 and the inner wall of the connection member 421, the gas is exhausted through the bypass exhaust tube 421a to the outside. Meanwhile, the remaining portion of the plasma generation gas flows into the space surrounded by the inner wall of the cylindrical portion 423a, as the dilution gas to be mixed with the sample gas.

While the plasma generation gas is flowing through the space between the inner wall of the external dielectric tube 411 and the outer wall of the internal dielectric tube 431 in the previously described manner, the high AC excitation voltage power source 415 is energized. The high AC excitation voltage power source 415 applies a low-frequency high AC voltage between the plasma generation electrodes, i.e. the ring-shaped electrode (high-voltage electrode) 412 and the dielectric coverage area (ground electrode) of the metallic tube 432. Consequently, an electric discharge occurs within the area sandwiched between the ring-shaped electrode 412 and the dielectric coverage area of the metallic tube 432. This electric discharge is induced through the dielectric coating layers (external dielectric tube 411 and internal dielectric tube 431), and therefore, is a dielectric barrier discharge. By this dielectric barrier discharge, the plasma generation gas flowing through the space between the inner wall of the external dielectric tube 411 and the outer wall of the internal dielectric tube 431 is ionized, forming a cloud of plasma (atmospheric-pressure non-equilibrium plasma).

The excitation light emitted from the atmospheric-pressure non-equilibrium plasma travels through the space between the inner wall of the external dielectric tube 411 and the outer wall of the internal dielectric tube 431 to the region where the sample gas is present, and ionizes the molecules (or atoms) of the sample component in the sample gas. The thereby generated sample ions are gathered to the ion-collecting electrode (i.e. the cylindrical portion 423a of the flanged metallic tube 423) due to the electric field created by the bias electrode (i.e. the exposed portion of the metallic wire 422) located directly above the sample-gas exit port, to be eventually detected as a current output. Consequently, an ion current corresponding to the amount of generated sample ions, i.e. an ion current corresponding to the amount of sample component, is fed to the current amplifier 428. The current amplifier 428 amplifies this current and provides it a detection signal. In this manner, the present Ar-BID produces a detection signal corresponding to the amount (concentration) of the sample component contained in the introduced sample gas.

In FIG. 5, the metallic wire 422 is made to function as the bias electrode, and the flanged metallic tube 423 is made to function as the ion-collecting electrode. Their functions may be transposed. That is to say, the metallic wire 422 may be connected to the current amplifier 428, and the flanged metallic tube 423 may be connected to the bias DC power source 427. It is also possible to replace the flanged metallic tube 423 with an element similar to the cylindrical metallic electrode 122 or 123 provided in the charge-collecting section in FIG. 1, and make this element function as the ion-collecting electrode or bias electrode.

Figure 11:
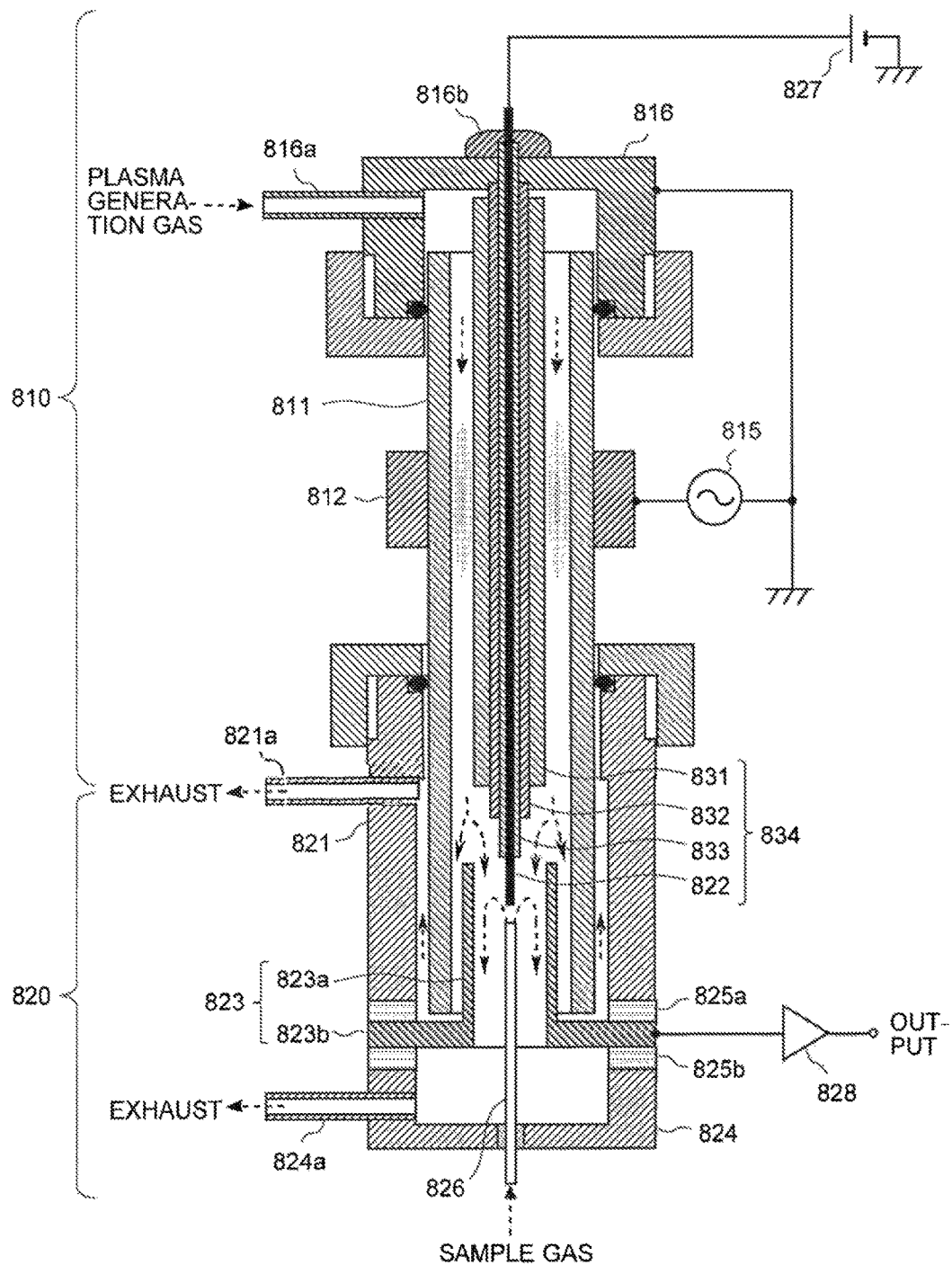
FIG. 11 is a schematic configuration diagram showing still another configuration example of conventional BIDs.

The basic components and detecting operation of the Ar-BID in the present embodiment are the same as those of the BID described in Patent Literature 3. FIG. 11 shows the configuration of the BID described in Patent Literature 3. In FIG. 1, the components which are common to FIGS. 5 and 11 are denoted by numerals whose last two digits are common to both figures.

The structural characteristics of the Ar-BID according to the present embodiment exist in the following points: the external dielectric tube 411 is made of a material whose surface resistivity or bulk resistivity (which are hereinafter simply and collectively referred to as the "resistivity") is lower than that of dielectric materials used in conventional Ar-BIDs (e.g. high-purity alumina, sapphire or quartz); the length of the dielectric coverage area (ground electrode) of the metallic tube 432 on the downstream side of the lower-end position of the ring-shaped electrode (high-voltage electrode) 412 is longer than the ground electrode length which allows creeping discharge (between the ring-shaped electrode 412 and the charge-collecting section 420) which depends on the resistivity; and the length of the dielectric coverage area (ground electrode) of the metallic tube 432 on the upstream side of the upper-end position of the ring-shaped electrode (high-voltage electrode) 412 is longer than the ground electrode length which allows creeping discharge (between the ring-shaped electrode 412 and the tube-line tip member 416) which depends on the resistivity. The resistivities of quartz, sapphire and high-purity alumina, which have been used as dielectric materials in conventional Ar-BIDs, are all approximately $1.0 \times 10^{14}$ Ωcm at normal temperature (about 20° C.). In the present embodiment, the external dielectric tube 411 is made of a dielectric material having a lower resistivity than the aforementioned value. Specifically, the cylindrical dielectric tube 411 in the present embodiment is made of a dielectric material whose resistivity at ordinary temperature is equal to or lower than $1.0 \times 10^{13}$ Ωcm. The length of the dielectric coverage area of the metallic tube 432 (ground electrode) on the downstream side of the position where the ring-shaped electrode 412 is provided is adjusted according to the aforementioned resistivity as well as such parameters as the frequency and amplitude of the low-frequency AC voltage, waveform of the power source and property of gas so that no creeping discharge will occur between the high-voltage electrode 412 and the charge-collecting section 420 (more specifically, for example, the lower-end area of the metallic tube 432 which is not covered with the internal dielectric tube 431, or the upper-end portion of the flanged metallic tube 423). Similarly, the length of the dielectric coverage area (ground electrode) of the metallic tube 432 on the upstream side of the position where the ring-shaped electrode 412 is provided is adjusted according to the aforementioned parameters so that no creeping discharge will occur between the high-voltage electrode 412 and the tube-line tip member 416. As the dielectric material whose resistivity is equal to or lower than $1.0 \times 10^{13}$ Ωcm, for example, an alumina material No. A445 or AH manufactured by Kyocera Corporation can be used. The internal dielectric tube 431 covering the metallic tube 432 may also be made of such a low-resistivity dielectric material, or it may be made of quartz, sapphire, high-purity alumina or other conventionally used materials.

In the Ar-BID according to the present embodiment, the ground electrode lengths which allow creeping discharge initiation between the ring-shaped electrode 412 and the charge-collecting section 420 as well as between the ring-shaped electrode 412 and the tube-line tip member 416 are shortened by using, as the material of the external dielectric tube 411, a dielectric material having a lower resistivity than that of dielectric materials used in conventional Ar-BIDs, and after that, the lengths of the dielectric coverage area of the metallic tube 432 on both upstream and downstream sides of the ring-shaped electrode 412 are made longer than the respective ground electrode lengths which allow creeping discharge initiation to impede the creeping discharge developing from the ring-shaped electrode 412 into both upstream and downstream sides. With this configuration, it is possible to improve the SN ratio of the Ar-BID while minimizing the increase in the detector size.

In the third embodiment described thus far, the lengths of the dielectric coverage area of the metallic tube 432 on both upstream and downstream sides of the ring-shaped electrode 412 are made longer than the respective ground electrode lengths which allow creeping discharge initiation. It is also possible to make only one of them, and particularly, only the length of the dielectric coverage area of the metallic tube 432 on the downstream side of the ring-shaped electrode 412, longer than the ground electrode length which allows creeping discharge (between the high-voltage electrode 412 and the charge-collecting section 420).

Fourth Embodiment

Figure 6:
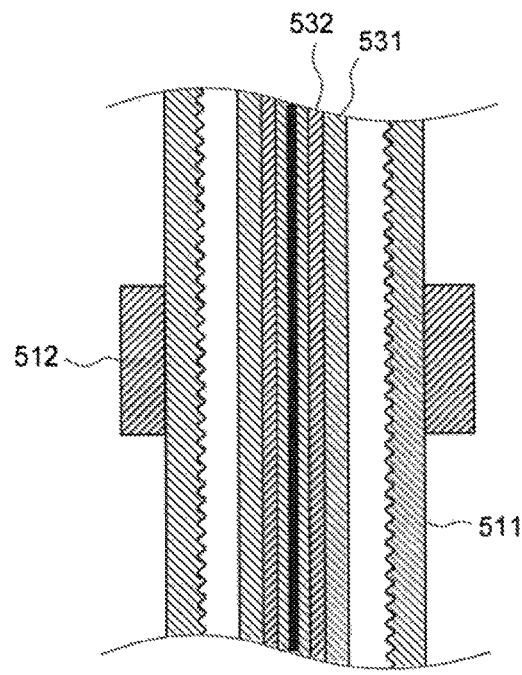
FIG. 6 is a partially enlarged view of an Ar-BID according to the fourth embodiment of the present invention.
Figure 7:
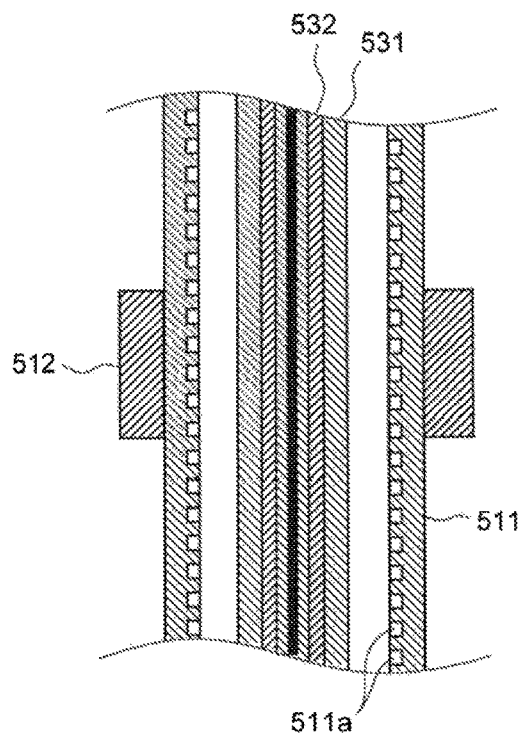
FIG. 7 is a partially enlarged view showing another configuration example of the Ar-BID according to the same embodiment.
Figure 8:
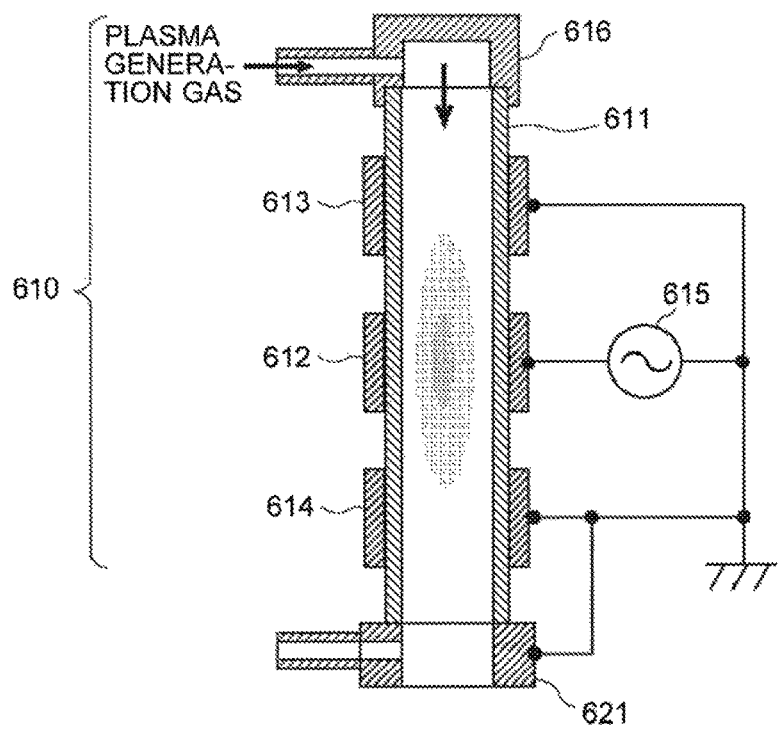
FIG. 8 is a schematic configuration diagram of the discharging section and surrounding area in a conventional BID.
Figure 9:
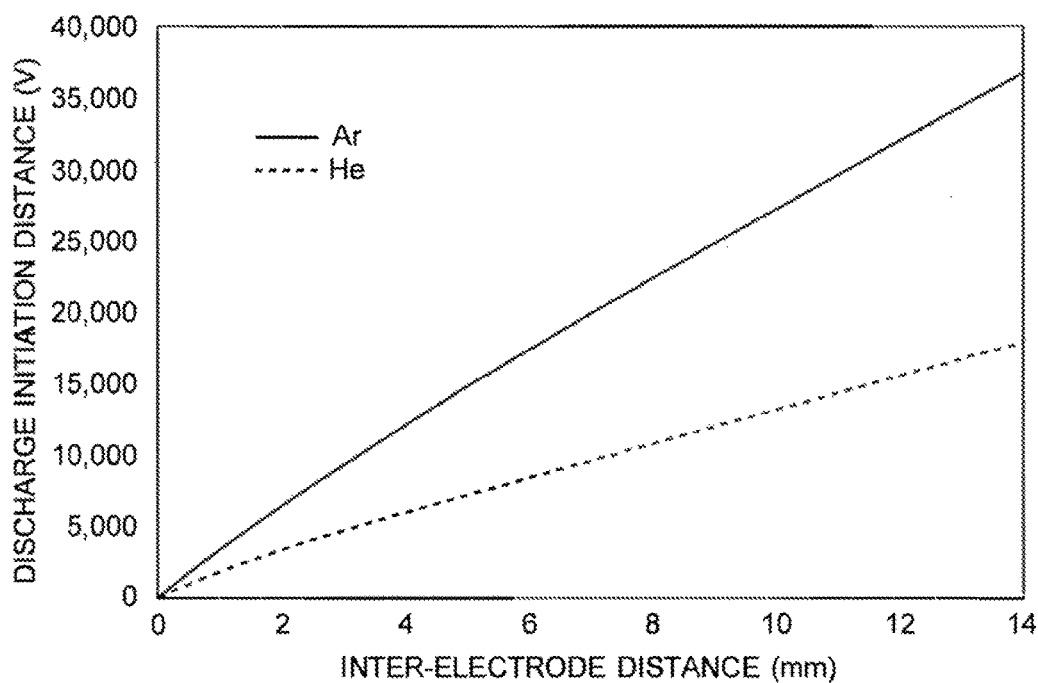
FIG. 9 is a graph showing the relationship between the discharge initiation voltage for spark discharge in Ar and He at atmospheric pressure and the inter-electrode distance.

FIGS. 6 and 7 are partially enlarged views each of which shows a configuration of the discharging section of the Ar-BID according to the fourth embodiment of the present invention. The overall configuration of the Ar-BID in the present embodiment is similar to the one shown in FIG. 5 and therefore will not be described.

The configuration of the Ar-BID in the present embodiment is identical to that of the third embodiment except that the ground electrode length which allows creeping discharge between the ring-shaped electrode (high-voltage electrode) 512 and the charge-collecting section and/or between the ring-shaped electrode 512 and the tube-line tip member (416 in FIG. 5) is shortened by forming an unevenness on the inner wall surface of the external dielectric tube 511. The external dielectric tube 511 may be made of a dielectric material used in conventional Ar-BIDs (quartz, sapphire or high-purity alumina) or a dielectric material having a low resistivity as in the third embodiment.

In order to form the unevenness, the inner wall surface of the external dielectric tube 511 is roughened in the example of FIG. 6, while a number of grooves 511a extending in a direction orthogonal to the longitudinal direction of the external dielectric tube 511 are formed on the inner wall surface of this external dielectric tube 511 in the example of FIG. 7. Those forms of unevenness needs be formed at least one of the following portions of the external dielectric tube 511: the inner circumferential surface of the area which covers the ring-shaped electrode 512 (this area is hereinafter called the "ring-shaped electrode coverage area"); the inner circumferential surface of the area located downstream of the ring-shaped electrode coverage area as well as upstream of the charge-collecting section (420 in FIG. 5; this area is hereinafter called the "downstream-side area"); and the inner circumferential surface of the area located upstream of the ring-shaped electrode coverage area as well as downstream of the tube-line tip member (this area is hereinafter called the "upstream-side area"). More preferably, the unevenness should be formed over the entire range of the inner circumferential surface of the external dielectric tube 511. When the unevenness is formed on the ring-shaped electrode coverage area and/or the downstream-side area, the ground electrode length which allows creeping discharge between the ring-shaped electrode 512 and the charge-collecting section becomes shorter. When the unevenness is formed on the ring-shaped electrode coverage area and/or the upstream-side area, the ground electrode length which allows creeping discharge between the ring-shaped electrode 512 and the tube-line tip member becomes shorter.

In the present embodiment, the length of the area covered with the internal dielectric tube 531, i.e. the dielectric coverage area (ground electrode), of the metallic tube 532 on the downstream side of the ring-shaped electrode 512 is adjusted according to the number and depth of the unevenness within the ring-shaped coverage area and the downstream-side area of the external dielectric tube 511 (i.e. the creepage distance between the ring-shaped electrode 512 and the charge-collecting section) as well as such parameters as the frequency and amplitude of the low-frequency AC voltage, waveform of the power source and property of gas so that no creeping discharge will occur between the ring-shaped electrode 512 and the charge-collecting section. Similarly, the length of the dielectric coverage area (ground electrode) of the metallic tube 532 on the upstream side of the ring-shaped electrode 512 is adjusted according to the number and depth of the unevenness within the ring-shaped coverage area and the upstream-side area (i.e. the creepage distance between the ring-shaped electrode 512 and the tube-line tip member) as well as the aforementioned parameters so that no creeping discharge will occur between the ring-shaped electrode 512 and the tube-line tip member.

In the Ar-BID according to the present embodiment, the ground electrode lengths which allow creeping discharge initiation are shortened by increasing the surface roughness of the inner surface of the external dielectric tube 511, and after that, the lengths of the dielectric coverage area (ground electrode) of the metallic tube 532 on both upstream and downstream sides of the ring-shaped electrode 512 are made longer than the respective ground electrode lengths which allow creeping discharge initiation so as to prevent the creeping discharge. With this configuration, it is possible to improve the SN ratio of the Ar-BID while minimizing the increase in the detector size.

In the fourth embodiment described thus far, the length of the dielectric coverage area (ground electrode) of the metallic tube 532 is made longer than the ground electrode lengths which allow creeping discharge initiation on both upstream and downstream sides of the ring-shaped electrode 512. It is also possible to make only one of them, and particularly, only the length of the dielectric coverage area of the metallic tube 532 on the downstream side of the ring-shaped electrode 512, longer than the ground electrode length which allows creeping discharge (between the ring-shaped electrode 512 and the charge-collecting section). In the case of thus making only the downstream-side length of the dielectric coverage area of the metallic tube 532 longer than the ground electrode length which allows creeping discharge, the unevenness is formed on the inner circumferential surface of at least either the ring-shaped electrode coverage area or the downstream-side area. In the case of making only the length of the dielectric coverage area of the metallic tube 532 on the upstream side of the ring-shaped electrode 512 longer than the ground electrode length which allows creeping discharge, the unevenness is formed on the inner circumferential surface of at least either the ring-shaped electrode coverage area or the upstream-side area.

REFERENCE SIGNS LIST 110, 310, 410 . . . Discharging Section
111, 211, 311 . . . Cylindrical Dielectric Tube
211a . . . Groove
112, 212, 312 . . . High-Voltage Electrode
113, 213, 313 . . . Upstream-Side Ground Electrode
114, 214, 314 . . . Downstream-Side Ground Electrode
115, 315, 415 . . . High AC Excitation Voltage Power Source
116, 416 . . . Tube-Line Tip Member
116a, 416a . . . Gas Supply Tube
120, 420 . . . Charge-Collecting Section
121, 421 . . . Connection Member
121a, 421a . . . Bypass Exhaust Tube
122 . . . Bias Electrode
123 . . . Collecting Electrode
124, 424 . . . Tube-Line End Member
124a, 424a . . . Sample Exhaust Tube
126, 426 . . . Sample Introduction Tube
127, 427 . . . Bias DC Power Source
128, 428 . . . Current Amplifier
412, 512 . . . Ring-Shaped Electrode
411, 511 . . . External Dielectric Tube
511a . . . Groove
434, 534 . . . Electrode Structure
422, 522 . . . Metallic Wire
431, 531 . . . Internal Dielectric Tube
432, 532 . . . Metallic Tube
433, 533 . . . Insulating Tube
423 . . . Flanged Metallic Tube

The invention claimed is:

1. A dielectric barrier discharge ionization detector for ionizing and detecting a sample component in a sample gas by using plasma induced by an electric discharge within a gas passage through which a plasma generation gas containing argon is passed, the detector comprising:
   a) a high-voltage electrode having a surface which faces the gas passage and is covered with a dielectric body;
   b) a ground electrode electrically connected to a ground and arranged so as to face the gas passage, the ground electrode having a surface which faces the gas passage and is covered with a dielectric body, with at least a portion of the surface being located downstream of the high-voltage electrode in a flow direction of the plasma generation gas;
   c) an AC power source connected to the high-voltage electrode, for applying an AC voltage between the high-voltage electrode and the ground electrode so as to induce a dielectric barrier discharge within the gas passage and thereby generate plasma; and
   d) a charge-collecting section forming a section of the gas passage and located downstream of the ground electrode, including a sample-gas introducer for introducing a sample gas into the downstream section and a collecting electrode for collecting ions generated from a sample component in the sample gas by light emitted from the plasma, where:
   a bulk resistivity or surface resistivity of the dielectric body covering the high-voltage electrode is equal to or lower than $1.0 \times 10^{13}$ Ωcm; and
   a length of the ground electrode on a downstream side of the high-voltage electrode is longer than an ground electrode length which allows creeping discharge between the high-voltage electrode and the charge-collecting section.

2. A dielectric barrier discharge ionization detector tfor ionizing and detecting a sample component in a sample gas by using plasma induced by an electric discharge within a gas passage through which a plasma generation gas containing argon is passed, the detector comprising:

a) a dielectric tube made of a dielectric material and containing an upstream section of the gas passage;
b) an electrically grounded tube-line tip member made of metal, for introducing the plasma generation gas into the dielectric tube;
c) a high-voltage electrode attached to an outer wall of the dielectric tube;
d) an electrically grounded upstream-side ground electrode attached to the outer wall of the dielectric tube and located upstream of the high-voltage electrode as well as downstream of the tube-line tip member in a flow direction of the plasma generation gas;
e) an electrically grounded downstream-side ground electrode attached to the outer wall of the dielectric tube and located downstream of the high-voltage electrode in the flow direction of the plasma generation gas;
f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and
g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:
a bulk resistivity or surface resistivity of the dielectric body covering the high-voltage electrode is equal to or lower than $1.0 \times 10^{13}$ Ωcm; and
one or both of following conditions are satisfied: a length of the upstream-side ground electrode in the flow direction is longer than an ground electrode length which allows creeping discharge between the tube-line tip member and the high-voltage electrode; or a length of the downstream-side ground electrode in the flow direction is longer than an ground electrode length which allows creeping discharge between the high-voltage electrode and the charge-collecting section.

3. A dielectric barrier discharge ionization detector for ionizing and detecting a sample component in a sample gas by using plasma induced by an electric discharge within a gas passage through which a plasma generation gas containing argon is passed, the detector comprising:
a) a dielectric tube made of a dielectric material and containing an upstream section of the gas passage;
b) a high-voltage electrode attached to an outer wall of the dielectric tube;
c) a ground electrode electrically connected to a ground and arranged so as to face the gas passage, the ground electrode having a surface which faces the gas passage and is covered with a dielectric body, with at least a portion of the surface being located downstream of the high-voltage electrode in a flow direction of the plasma generation gas;
d) an AC power source connected to the high-voltage electrode, for applying an AC voltage between the high-voltage electrode and the ground electrode so as to induce a dielectric barrier discharge within the gas passage and thereby generate plasma; and
e) a charge-collecting section forming a downstream section of the gas passage and located downstream of the ground electrode, including a sample-gas introducer for introducing a sample gas into the downstream section and a collecting electrode for collecting ions generated from a sample component in the sample gas by light emitted from the plasma, where:
an unevenness is formed on an inner wall of the dielectric tube over an area where the high-voltage electrode is attached and/or an area located downstream of the aforementioned area and upstream of the charge-collecting section; and
a length of the ground electrode on a downstream side of the high-voltage electrode is longer than an ground electrode length which allows creeping discharge between the high-voltage electrode and the charge-collecting section.

4. A dielectric barrier discharge ionization detector for ionizing and detecting a sample component in a sample gas by using plasma induced by an electric discharge within a gas passage through which a plasma generation gas containing argon is passed, the detector comprising:
a) a dielectric tube made of a dielectric material and containing an upstream section of the gas passage;
b) an electrically grounded tube-line tip member made of metal, for introducing the plasma generation gas into the dielectric tube;
c) a high-voltage electrode attached to an outer wall of the dielectric tube;
d) an electrically grounded upstream-side ground electrode attached to the outer wall of the dielectric tube and located upstream of the high-voltage electrode as well as downstream of the tube-line tip member in a flow direction of the plasma generation gas;
e) an electrically grounded downstream-side ground electrode attached to the outer wall of the dielectric tube and located downstream of the high-voltage electrode in the flow direction of the plasma generation gas;
f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and
g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:
an unevenness is formed on an inner wall of the dielectric tube over an area where the high-voltage electrode is attached and/or an area located downstream of the aforementioned area and upstream of the charge-collecting section; and
a length of the downstream-side ground electrode is longer than an ground electrode length which allows creeping discharge between the high-voltage electrode and the charge-collecting section.

5. A dielectric barrier discharge ionization detector for ionizing and detecting a sample component in a sample gas by using plasma induced by an electric discharge within a gas passage through which a plasma generation gas containing argon is passed, the detector comprising:
a) a dielectric tube made of a dielectric material and containing an upstream section of the gas passage;

b) an electrically grounded tube-line tip member made of metal, for introducing the plasma generation gas into the dielectric tube;

c) a high-voltage electrode attached to an outer wall of the dielectric tube;

d) an electrically grounded upstream-side ground electrode attached to the outer wall of the dielectric tube and located upstream of the high-voltage electrode as well as downstream of the tube-line tip member in a flow direction of the plasma generation gas;

e) an electrically grounded downstream-side ground electrode attached to the outer wall of the dielectric tube and located downstream of the high-voltage electrode in the flow direction of the plasma generation gas;

f) an AC power source connected to the high-voltage electrode, for applying an AC voltage between the high-voltage electrode and the upstream-side ground electrode as well as between the high-voltage electrode and the downstream-side ground electrode so as to induce a dielectric barrier discharge within the gas passage and thereby generate plasma; and g) a charge-collecting section forming a downstream section of the gas passage and located downstream of the downstream-side ground electrode, including a sample-gas introducer for introducing a sample gas into the downstream section and a collecting electrode for collecting ions generated from a sample component in the sample gas by light emitted from the plasma, where:

an unevenness is formed on an inner wall of the dielectric tube over an area where the high-voltage electrode is attached and/or an area located upstream of the aforementioned area and downstream of the tube-line tip member; and a length of the upstream-side ground electrode is longer than an ground electrode length which allows creeping discharge between the high-voltage electrode and the tube-line tip member.

* * * * *